United States Patent
Nioutsikou

(10) Patent No.: US 10,821,302 B2
(45) Date of Patent: Nov. 3, 2020

(54) METHOD FOR ACQUIRING MAGNETIC RESONANCE IMAGE DATA FOR IMAGE-GUIDED RADIOTHERAPY

(71) Applicant: Siemens Healthcare GmbH, Erlangen (DE)

(72) Inventor: Elena Nioutsikou, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 16/359,064

(22) Filed: Mar. 20, 2019

(65) Prior Publication Data

US 2019/0290932 A1    Sep. 26, 2019

(30) Foreign Application Priority Data

Mar. 20, 2018 (EP) ................... 18162807

(51) Int. Cl.
| | | |
|---|---|---|
| G01V 3/00 | (2006.01) | |
| A61N 5/10 | (2006.01) | |
| A61B 90/00 | (2016.01) | |
| A61B 5/055 | (2006.01) | |
| G01R 33/48 | (2006.01) | |
| G01R 33/54 | (2006.01) | |

(52) U.S. Cl.
CPC ............ *A61N 5/1039* (2013.01); *A61B 5/055* (2013.01); *A61B 90/37* (2016.02); *A61N 5/1049* (2013.01); *G01R 33/4808* (2013.01); *G01R 33/546* (2013.01); *A61B 2090/374* (2016.02); *A61N 2005/1055* (2013.01); *A61N 2005/1061* (2013.01)

(58) Field of Classification Search
CPC .. G01R 33/441; G01R 33/3415; G01N 24/08; G01N 24/084; B82Y 10/00
USPC ........................................................ 324/300
See application file for complete search history.

(56) References Cited

U.S. PATENT DOCUMENTS

| | | | |
|---|---|---|---|
| 9,878,178 B2 | 1/2018 | Schweizer | |
| 2005/0088177 A1 | 4/2005 | Schreck et al. | |
| 2012/0063566 A1* | 3/2012 | Smith .................... | A61B 6/025 378/37 |
| 2014/0088984 A1 | 3/2014 | Oh et al. | |

(Continued)

FOREIGN PATENT DOCUMENTS

DE    102014217283 A1    3/2016

OTHER PUBLICATIONS

D. Jaffray et. al.: "MReadings: MR in RT", Contributions from our Magnetom users, 3rd Edition Estro 2017, Siemens Healthcare GmbH, Pub. Nr. A91MR-1100-88C-7600; 2017.

(Continued)

*Primary Examiner* — Walter L Lindsay, Jr.
*Assistant Examiner* — Frederick Wenderoth
(74) *Attorney, Agent, or Firm* — Schiff Hardin LLP

(57) ABSTRACT

In a method for acquiring magnetic resonance raw data for image-guided radiotherapy, a number of imaging goals are provided to a computer. For each imaging goal, a magnetic resonance imaging protocol is selected. For each selected magnetic resonance imaging protocol, a number of parameters for that protocol are adjusted according to the respective imaging goal. The resonance raw data are acquired with the magnetic resonance imaging protocol and their parameters.

7 Claims, 2 Drawing Sheets

(56) References Cited

U.S. PATENT DOCUMENTS

| | | | | |
|---|---|---|---|---|
| 2015/0125057 A1* | 5/2015 | Huddleston | ............ | A61B 5/055 |
| | | | | 382/131 |
| 2016/0059041 A1 | 3/2016 | Grodzki et al. | | |
| 2016/0082285 A1 | 3/2016 | Grodzki et al. | | |
| 2016/0213947 A1* | 7/2016 | Han | ........................ | G06T 7/246 |
| 2016/0217595 A1* | 7/2016 | Han | ..................... | G06T 7/0012 |

OTHER PUBLICATIONS

Siemens Healthcare GmbH:"MRi in Radiation Therapy" Peer-to-peer exchange of protocols, articles and Tips, https://www.healthcare.siemens.com/magnetic-resonance-imaging/magnetom-world/hot-topics/mri-in-radiation-therapy, 2018.

Y. Cao et. al.: "MR-integrated Workflows in Radiation Therapy" for Magnetom Systems, Siemens Healthcare GmbH, 2017, Pub. Nr. A91MR-1100-89C-7600; 2017.

European Search Report dated Oct. 19, 2018, in Application No. 18162807.4-1022.

* cited by examiner

METHOD FOR ACQUIRING MAGNETIC RESONANCE IMAGE DATA FOR IMAGE-GUIDED RADIOTHERAPY

BACKGROUND OF THE INVENTION

Field of the Invention

The present invention concerns a method for acquiring magnetic resonance image data for image-guided radiotherapy. The present invention also concerns a computer and a non-transitory, computer-readable data storage medium encoded with programming instructions.

Description of the Prior Art

Radiation therapy (radiotherapy, RT) is typically used to treat a patient's disease, in particular cancer. For that purpose, a target volume containing tumor cells or malignant cells is radiated with ionizing radiation. Within the treatment, the radiation therapy is either used by itself or in combination with other forms of treatment such as chemotherapy or surgery. Furthermore, the ionizing radiation is either delivered from outside the patient's body (external-beam radiation therapy) or, alternatively, a radiation source is placed within the patient's body (internal radiation therapy, brachytherapy), in particular in the target volume.

In order to avoid irradiation of tissue around the target volume, in particular organs at risk, and in order to deliver a radiation dose into the target volume, which is sufficient to kill or damage the tumor cells or the malignant cells, preferably 3-dimensional medical images of the patient and especially of the target volume are used to plan the irradiation. This is known as image-guided radiotherapy, with medical images being acquired by an x-ray computed tomography scanner (CT-scanner), for example.

Preferably however, those medical images are acquired by a magnetic resonance imaging scanner (MRI-scanner). The use of an MRI-scanner provides a comparatively high soft tissue contrast, which, for example, facilitates a classification of cancer tissue and the determination of the shape for delineation of the target and/or of an organ at risk (OAR).

In order to produce a magnetic resonance image, raw MR data must be acquired, from which the image (image data) is reconstructed, for a given imaging goal (purpose), such as the determination of an organ at risk delineation, the study of a tumor diffusion or a motion analysis. Such raw data acquisition is a comparatively complex task. This is because a number of (magnetic resonance imaging) protocols can be used for acquiring raw data and reconstructing the image for a given imaging goal. Furthermore the appearance and characteristics, e.g. a slice thickness, resolution, or contrast to noise ratio, of the magnetic resonance image varies for each protocol and for parameters such as a field of view (FOV), the receiver bandwidth or matrix size, used within a particular protocol.

The education of radiation therapy staff, such as radiation oncologists or physicists, typically doesn't involve sufficient training in magnetic resonance imaging. Radiologists, who are trained in magnetic resonance imaging, typically have no or not sufficient education in radiation therapy. Consequently, protocols and/or the parameters may be used for acquiring a magnetic resonance image or image data that are not suited for the respective imaging goal, and an (systematic) error can be introduced in the image-guided radio therapy process. This can result in a less effective treatment of the patient's disease and, consequently, in a less effective or even detrimental therapeutic result.

MR-based methods to support the planning of the irradiation of a patient are known from US 2016/0082285 A1 and U.S. Pat. No. 9,878,178 B2, for example.

SUMMARY OF THE INVENTION

An object of the present invention is to support the planning of the irradiation of a patient in radiation therapy by magnetic resonance imaging. Furthermore, it is an object of the present invention to provide a computer and a non-transitory, computer-readable data storage medium encoded with programming instructions for executing such a method.

The method is used for acquiring magnetic resonance raw data for image-guided radiotherapy. From the magnetic resonance raw data, MR image data are reconstructed that form a magnetic resonance image or a number of images.

In a first step of the inventive method, electronic inputs representing (designating) a number of imaging goals (purposes, objects) are provided to a computer. In particular, the imaging goals are provided by a user such as radiation therapy staff. Herein, a number of imaging goals is understood to be one imaging goal or more than one imaging goal.

In a second step, for each imaging goal, a magnetic resonance imaging protocol, hereinafter simply referred to as a protocol, is selected by the computer. The protocol is selected so as to comply with the respective imaging goal. In other words, the selected protocol is suited to accomplish (fulfill) the respective imaging goal. In a third step, for each selected protocol, a number of parameters for the selected protocol are adjusted by the computer according to the respective imaging goal. Subsequently, in a fourth step, the magnetic resonance raw data are acquired with the protocol and with those parameters.

Preferably, in the fourth step, post-acquisition activities such as distortion correction, and reconstruction of images to a transverse plane, are performed. For example, the images are then used in a treatment planning system, in particular for image-guided radiotherapy, or in a contouring system to determine a contour of a target such as a tumor.

A protocol is composed of a number of so called sequences, wherein a number of sequences is understood to mean one sequence or more than one sequence. The sequences are a particular setting of the chronological order of pulses of radio waves and pulsed field gradients for the acquisition of raw MR data, from which the respective image (image data) is determined or reconstructed. The respective image is a three-dimensional volume representation of the examined volume or a two-dimensional plane (slice) representation of the examined volume. The appearance of the determined or reconstructed image varies dependent of the sequence that is used. For example, the appearance of fatty tissue in the respective reconstructed image is comparatively light for a T1-weighted sequence and comparatively dark for a T2-weighted sequence.

Protocols can be combined if they share sequences and parameters. Advantageously, by this means, a total time necessary for the acquisition of the image data for all respective imaging goals is reduced.

The parameters are selectable or adjustable quantities either of the sequence or of the image reconstructed by the image data. For example, a parameter can be a receiver bandwidth, a flip angle in a sequence, an acquisition time for a sequence, a field of view, a matrix size of the acquired image, or a number of slices.

The imaging goal does not contain information about a protocol or parameters used for acquiring raw data for image-guided radiotherapy. Rather, the imaging goal is a designated purpose, object or objective, which the image and thus the image data should fulfill (satisfy), such that the planning of the image-guided radiation therapy is supported or facilitated. The imaging goal is provided by the radiation oncology staff. For example, the imaging goal may be the determination of a target delineation, the determination of organ at risk delineation, the determination of brachytherapy applicator delineation or an analysis of target motion. The imaging goal is selected from a list, or provided as a plain text file, and is further provided to the computer as an input.

The inventive method makes it relatively simple, especially for an inexperienced user of a magnetic resonance imaging scanner (MRI-scanner), to select and use a protocol and parameters for the protocol, which are suited to comply with the imaging goal. Consequently, systematic errors in the planning and execution of image-guided radiotherapy are avoided, such errors arising in particular from a lack of training in the use of MRI-scanners for radiation therapy.

In an embodiment, a database is provided. The database contains information that assign a magnetic resonance imaging protocol, and a number of the parameters for that protocol, to each of a number of imaging goals. In other words, to each of a number of imaging goals a protocol and parameters for that protocol are linked. In particular, the database contains a list of imaging goals, with a protocol, preferably one, or an identification for a protocol, linked to each imaging goal in the list. Further, the parameters for the protocols are linked to the respective protocols in the database. Preferably, the information in the database has been obtained empirically, for example, by experienced staff, who used the protocol and the parameters for the protocol for fulfilling the respective imaging goal. Consequently, the expertise and knowledge of the members of staff concerning the use of MRI-scanners is made available to other user via the database.

In another embodiment, in the second step, the protocol is selected dependent on the respective imaging goal by use of the database. For this purpose the database is searched by the computer for the respective imaging goal, and the protocol assigned (linked) to that imaging goal is returned. The returned protocol thus complies with (fulfills) the imaging goal. Thus, the protocol complying with the respective imaging goal is selected solely by "knowledge" of the imaging goal.

Preferably, within the step of selecting the protocol, after the protocol is returned from the database, the user confirms or discards the selection of the respective protocol. Additionally, when more than one protocol is returned for a given imaging goal, the user is offered a choice among those protocols.

Within the third step, i.e. within adjusting the parameters for the respective protocol for the given imaging goal, each imaging goal is converted (translated) into a number of first metrics and a range (interval) for each of the first metrics. Therein, a first metric represents a measure (quantity), which especially is determinable by means of the image, wherein the first metric quantitatively assesses (evaluates, describes) the respective imaging goal. For example, the first metric is a contrast to noise ratio (CNR) between target and surrounding tissue, a slice thickness of the image or an in-plane-resolution. The range for the first metric is for example expressed by a maximum or a minimum value of said first metric. For example, a range for the slice thickness ranging from of a minimally feasible value, such as 0.1 mm, to 2 mm is expressed by a maximum value of 2 mm for the slice thickness. For example, for the conversion, a table is provided, which assigns an imaging goal to one first metric and a range for said first metric. This table is stored in the database. A user can provide limits for the range of the first metrics, additionally. For example, the user manually sets a maximum slice thickness of 1 mm, in particular via a user interface of the computer.

According to a further embodiment, boundary conditions are provided and the range of each of the first metrics, which were obtained by converting the respective imaging goals, is adjusted to said boundary conditions. The boundary conditions represent available equipment or patient characteristics. With the boundary conditions, limits (restrictions) for the range of the first metrics are derived. Adjusting the range of the first metric in other words means that limits corresponding to the boundary conditions are applied to the range of the respective first metric. For example, the boundary conditions are selected from a list, or provided as a plain text file, and are also provided to the computer. The boundary conditions can represent available equipment, for example a type or a number of RF coils, a number of available RF channels, what kind of MRI-scanner is used for acquiring the raw data, the magnet strength of the MRI-scanner. Alternatively or additionally, the boundary conditions can represent patient tolerance to (scan) acquisition time, or missing anatomy of the patient.

Furthermore, within the third step of the method for acquiring image data for image-guided radiotherapy, the parameters, that are assigned to the respective protocol in the database are obtained from the database. In other words the parameters are retrieved from the database, wherein these parameters are linked to the respective protocol and imaging goal.

Subsequently, a second metric is determined as a function of the parameters. Alternatively, a second metric and a range for the second metric is determined. The second metric represents an expected first metric for using the parameters for acquiring the respective image data. In other words, the second metrics are first metrics that are predicted or forecast for obtaining (acquiring) raw data with the parameters. In particular the computer determines a second metric by calculation using physical models, physical laws and/or are predicted by simulations. Preferably, for each first metric, one respective second metric is determined. Thus, the number of first metrics and the number of second metrics are equal. For example, for a contrast to noise ratio as a first metric, a contrast to noise ratio is determined as a second metric.

Subsequently, the range of each of the first metrics is compared to the respective second metric or, alternatively, to the range of the respective second metric. By comparing the range of the first metric to the respective (predicted) second metric, it is possible to verify if parameters for a protocol comply with the imaging goal and the boundary conditions. If the range of one of the first metrics and the respective second metric do not comply, i.e. if the value determined for second metric is not within the range of the respective first metric, or if a range determined for the second metric does not overlap with the range of the respective first metric, the parameters are changed. Alternatively, the parameters are only changed if a number of second metrics do not comply with the range of the respective first metric. Preferably, the parameters are changed according to an iterative, nonlinear optimization-algorithm. For example, an algorithm using Newton's method or an algorithm using a Quasi-Newton method is used.

Alternatively, parameters are changed according to a machine learning algorithm or according to an artificial neural network or are determined by means of such a machine learning algorithm or by means of such an artificial neural network.

This third step is necessary because the parameters retrieved from the database have been used to satisfy certain boundary conditions, which can differ from the current boundary conditions.

In summary, the parameters for the selected protocols are adjusted such that they comply with the imaging goal, wherein boundary conditions are taken into account. Preferably, the user confirms or alters the determined parameters. Additionally, the selected protocol and the parameters for the protocol can be stored, e.g. in the database, and thereby used for follow-up examination of the patient without having to select the protocol or adjusting the parameters. Thus, reproducibility and comparability of the examinations of the patient is facilitated.

In another embodiment of the method for acquiring raw data for image-guided radiotherapy, information is stored in the database that assigns (selected) protocols and (adjusted) parameters used for acquiring the magnetic resonance raw data to the respective imaging goal.

Thus the database is extended. Using the information stored in the database, a second alternative protocol and parameters for this second protocol are assigned to the respective imaging goal. Consequently, more than one protocol is assigned to the respective imaging goal. For example, the database further assigns the respective protocol to an institution or to a person who stored the information. It is then possible for a user of the database to choose between alternative protocols for one imaging goal based on the institution or person who has stored the respective information. Moreover, a user is offered the opportunity to store information in the database based on the quality of the resulting image.

The computer contains a controller or processor for executing the method described above. The computer can be a single work station or a personal computer. Alternatively, the computer is a server or embodies one or more clustered computing devices.

The computer further has an interface to the MRI-scanner. Thus, it is possible to use selected protocol and the parameters for the protocols for the acquisition of the raw data by the MRI-scanner.

A database system according to the invention has a computer readable storage device, on which the database is stored. The database contains information that assigns a magnetic resonance imaging protocol and parameters for that protocol to each of a number of imaging goals.

Furthermore, the database system has an interface to the computer. Therein, the database system preferably is or includes a server. The database system is for example used within one institution or one department of said institution. Consequently, the database, and in particular the extension of the database by storing information, is only available within the institution or department. Alternatively, the database system is used for a number of institutions. With other words, the database system is a shared (global) database system. For example, the name or an identification of the institution, which created and/or used the protocol and the parameters for the protocols for a given purpose and additionally or alternatively stored the respective information in the database, is linked to the information in the database. Consequently, it is possible for a user of the database system to choose a protocol and the parameters for the protocol for a given imaging goal dependent on the name of the institution, which created and/or stored the information in the database.

The present invention also concerns a non-transitory, computer-readable data storage medium encoded with programming instructions that, when the storage medium is loaded into a computer, cause the computer to implement any or all embodiments of the method according to the invention, as described above.

DESCRIPTION OF THE PREFERRED EMBODIMENTS

Figure 1:
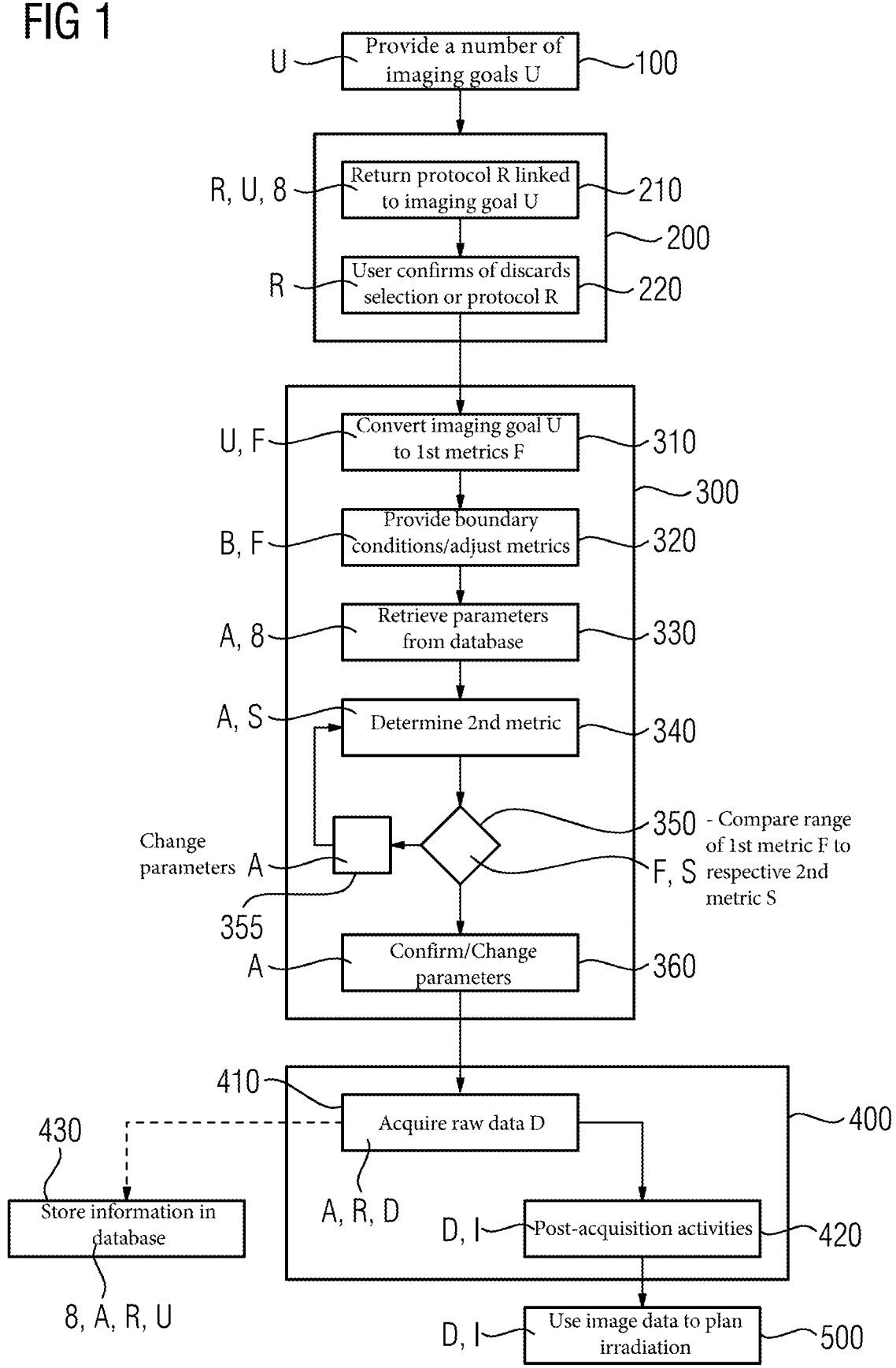
FIG. 1 is shows a flowchart schematically illustrating an embodiment of the method for acquiring magnetic resonance raw data for image-guided radiotherapy, wherein a number of imaging goals are provided and for each imaging goal a magnetic resonance imaging protocol is selected and parameters for said protocols are determined.

The flowchart diagram of FIG. 1 illustrates a method for acquiring (magnetic resonance) raw data D for image guided radiotherapy, wherein the raw data are used for the reconstruction of one (magnetic resonance) image I or a number of images I.

Within a first step 100 of the method, a number of imaging goals U are provided. The imaging goals U are provided by a user such as a radiation oncologist. Herein, a number of imaging goals U is understood to be one imaging goal U or more than one imaging goal U. The imaging goal U is selected from a list. For this purpose a computer 2 has a display device 4 and an input device 6, which according to this embodiment are a computer screen and a keyboard. The imaging purpose U can be the determination of a tumor delineation of the gross target volume (GTV), an organ at risk delineation of bladder, rectum and pelvic bones or a synthetic CT generation.

In a second step 200, for each imaging goal U a magnetic resonance imaging protocol (protocol R), is selected, wherein the protocol R is suited to accomplish the imaging goal U. For this purpose, a database 8 is provided, wherein the database 8 contains information that assigns, to each of a number of imaging goals U, a protocol R and parameters A for that protocol R. According to this embodiment, the database 8 contains a list of imaging goals U, wherein a protocol R, preferably one, is linked to each imaging goal U in the list. Further, the parameters A for the protocols R are linked to the respective protocols R in the database 8.

Within the second step 200, the database 8 is searched for the respective imaging goal U and the protocol assigned (linked) to said imaging goal U is returned (step 210). In summary, the protocol R complying with the respective imaging goal U is selected solely by the imaging goal U. For example, for the imaging goal U "the determination of a target delineation of the gross target volume (GTV)" a protocol comprising the sequence "T2 SPACE 3D" is selected.

Subsequently within the second step 200, the user confirms or discards the selection of the respective protocol R (step 220). In case that more than one protocol R is returned for a given imaging goal U, the user chooses between said protocols R.

Each protocol R is composed of a number of sequences, wherein a number of sequences is understood to mean one sequence or more than one sequence. In an alternative embodiment of the method, protocols R are combined subsequently to step 220, if they share sequences and parameters.

In a third step 300, for each selected protocol R, a number of parameters A for said selected protocol R are adjusted according to the respective imaging goal U.

Within this third step 300, each imaging goal U is converted into a number of first metrics F such as a value of a (isotropic) voxel size or a value of a slice thickness and into a range for each of the first metrics F (step 310).

In a not shown alternative, the user manually provides limits for the range of the first metrics F via the input device 6 and the display device 4.

Subsequently, in step 320, boundary conditions B are provided and the range of each first metric is adjusted dependent on said boundary conditions B. For this purpose, limits (restrictions) for the range of the first metrics F are derived from the boundary conditions B. The limits are applied to the respective first metric F. The boundary conditions B are selected from a list via the input device 6 and the display device 4 of the computer 2 and provided to the computer 2.

In a not shown alternative embodiment, steps 310 and 320 are executed between the first step 100 and the second step 200.

Furthermore, within the third step 300, the parameters are retrieved from the database, wherein those parameters A are retrieved from the database 8 (step 330), which are linked to the respective selected protocol R and imaging goal U. In a not shown alternative embodiment of the invention, said parameters A are retrieved from the database 8 within step 200.

In a subsequent step 340, for each first metric F a corresponding second metric S is determined as a function of the retrieved parameters A, the second metrics S are the result of a calculation or prediction of the first metrics F by means of physical models, physical laws or a simulation for obtaining raw data D with said parameters A and the corresponding protocol R.

In a comparing step 350, the range of each of the first metrics F is compared to the respective second metric S. If the range of the first metric F and the calculated respective second metric S do not comply, the parameters A are changed (step 355) and the second metrics S are determined as a function of the changed (altered) parameters A. For this purpose, an optimization algorithm using Newton's method or alternatively another optimization algorithm, which for example uses a Quasi-Newton method, is used.

According to not shown alternative embodiments, the parameters are changed according to a machine learning algorithm or by means of a neural network.

In a subsequent step 360, the parameters A are confirmed by the user or alternatively are changed manually by said user. However, by the display device 4, the user is given instructions, which parameters A should be kept at a fixed value or within what range the parameter A can be changed such that the imaging goal U is still accomplished.

In a fourth step 400, the magnetic resonance raw data D are acquired with said protocols R and with the parameters A (step 410). Subsequently, post-acquisition activities such as distortion correction or the reconstruction of images I, are performed by the computer 2 (step 420).

In a facultative step 430, information, which assigns protocols R and parameters A used for acquiring the magnetic resonance raw data D to the respective imaging goal U, is stored in the database 8. The database 8 is thereby extended.

In a fifth step 500, the image data transferred from the raw data D and/or the reconstructed images I, are used for planning an irradiation of a patient. For this purpose said image data and/or the images I are provided to a radiation oncologist or alternatively or additionally to a planning system.

Figure 2:
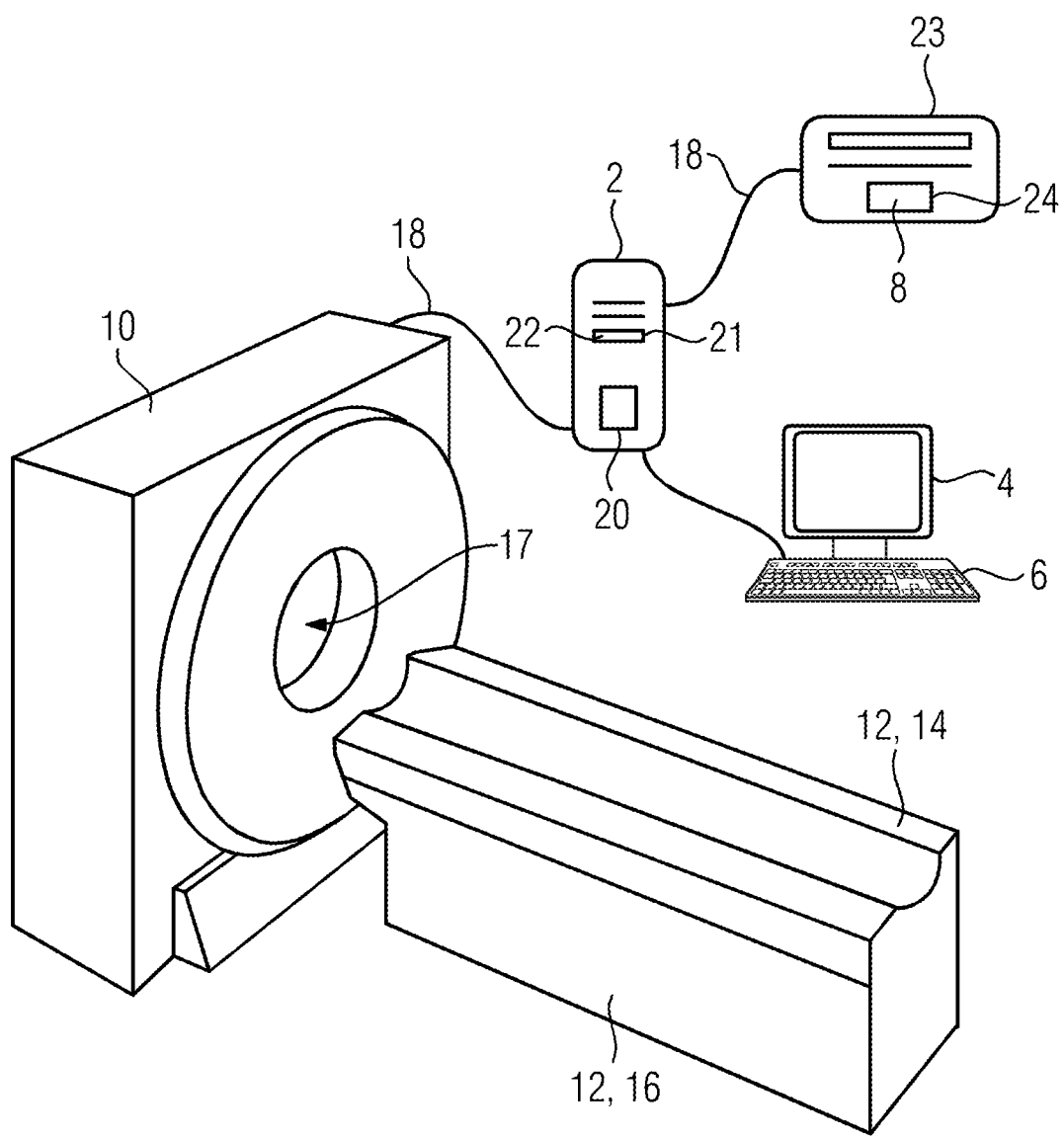
FIG. 2 shows magnetic resonance imaging scanner for acquiring magnetic resonance image data, wherein the magnetic resonance imaging scanner is connected to a processing device comprising a controller as well as an interface to a database system.

FIG. 2 shows a magnetic resonance imaging scanner (MRI scanner) 10, by which means the raw data D and images I of a patient are acquired. The images data D are acquired by a method illustrated by the flowchart diagram of FIG. 1. Further, a patient table 12 is shown, wherein a top plate 14 of the patient table 12 is movable relative to a base 16 of the patient table. A patient lying on the patient table 12 thus can be brought into a tunnel-shaped acquisition area 17 of the MRI-scanner 10.

The MRI-scanner 10 is further connected to the computer 2. The computer 2 has an interface 18 to the MRI-scanner 10. It is thereby possible to carry out the acquisition of the raw data D according to the method described in FIG. 1, i.e. the MRI-scanner 10 performs the acquisition of the raw data D with the protocols R selected by the method and with adjusted parameters A for the protocols R according to the method.

The computer 2 has a controller 20 for executing the method. The controller 20 is a microprocessor an ASIC (application specific integrated circuit) or a FPGA (field programmable gate array). The computer 2 is depicted as a single work station. Alternatively, the computer 2 is a server or is formed by one or more clustered computing devices.

The computer 2 has a computer readable storage device 21 such as a hard disk, on which a computer program code 22 is encoded. The program code 22 cause the method described above to be executed by the controller 20 of the computer 2.

The computer 2 further has an interface 18 to a database system 23, which according to this embodiment of the invention is a server. The database system has a computer readable storage device 24 such as a hard disk, on which the database 8 is stored. This database system is suited to be connected (interfaced) to a number of computer 2, for example by the internet, such that user of those multiple computers 2 share the database 8.

In an alternative embodiment, the computer 2 is included in the database system 23. The database system 23 contains a computer readable storage device 24.

Via the display device 4, further instructions are provided for a user of the MRI-Scanner 10. For example, such an instruction is a rate of a contrast medium injection into the patient and/or the preferred sequence when the contrast medium should be injected.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for acquiring magnetic resonance raw data for image-guided radiotherapy, said method comprising:
   providing electronic inputs into a computer that respectively designate different imaging goals that are needed to be achieved in order to support image-guided radiotherapy;
   via said computer:
      for each imaging goal from among the different imaging goals, selecting a magnetic resonance imaging protocol comprising a plurality of protocol parameters;
      accessing a database comprising information that assigns respective magnetic resonance imaging protocols, and the protocol parameters thereof, to each of a plurality of imaging goals;
      selecting said at least one magnetic resonance imaging protocol using said information in said database;
      converting each imaging goal into a plurality of first metrics and a range for each of said first metrics;
      obtaining the protocol parameters assigned to the selected magnetic resonance imaging protocol from said database;
      determining a plurality of second metrics dependent on the protocol parameters obtained from said database, each second metric representing a calculated prediction of a corresponding first metric associated with the use of said protocol parameters obtained from said database;
      comparing a range of each first metric with a range of the respective second metric determined therefrom;
      adjusting the protocol parameters obtained from the database if one of said second metrics does not comply with the range of the respective first metrics from which said second metric was determined;
      operating a magnetic resonance data acquisition scanner so as to execute at least one selected magnetic resonance imaging protocol in order to acquire magnetic resonance raw data from a subject using the protocol parameters of said at least one selected magnetic resonance image protocol; and
      transforming said acquired raw magnetic resonance data into magnetic resonance image data so as to reconstruct a magnetic resonance image that is needed for said image-guided radiotherapy.

2. A computer comprising:
   an input interface that receives electronic inputs that respectively designate different imaging goals that are needed to be achieved in order to support image-guided radiotherapy;
   a processor configured to:
      select, for each imaging goal from among the different imaging goals, a magnetic resonance imaging protocol comprising a plurality of protocol parameters;
      access a database comprising information that assigns respective magnetic resonance imaging protocols, and the protocol parameters thereof, to each of a plurality of imaging goals;
      select said at least one magnetic resonance imaging protocol using said information in said database;
      convert each imaging goal into a plurality of first metrics and a range for each of said first metrics;
      obtain the protocol parameters assigned to the selected magnetic resonance imaging protocol from said database;
      determine a plurality of second metrics dependent on the protocol parameters obtained from said database, each second metric representing a calculated prediction of a corresponding first metric associated with the use of said protocol parameters obtained from said database;
      compare a range of each first metric with a range of the respective second metric determined therefrom;
      adjust the protocol parameters obtained from the database if one of said second metrics does not comply with the range of the respective first metrics from which said second metric was determined;
      operate a magnetic resonance data acquisition scanner so as to execute at least one selected magnetic resonance imaging protocol in order to acquire magnetic resonance raw data from a subject using the protocol parameters of said at least one selected magnetic resonance image protocol; and
      transform said acquired raw magnetic resonance data into magnetic resonance image data so as to reconstruct a magnetic resonance image that is needed for said image-guided radiotherapy.

3. A non-transitory, computer-readable data storage medium encoded with programming instructions, said storage medium being loaded into a computer and said programming instructions causing said computer to:
   receive electronic inputs that respectively designate different imaging goals that are needed to be achieved in order to support image-guided radiotherapy;
   for each imaging goal from among the different imaging goals, select a magnetic resonance imaging protocol comprising a plurality of protocol parameters;
   access a database comprising information that assigns respective magnetic resonance imaging protocols, and the protocol parameters thereof, to each of a plurality of imaging goals;
   select said at least one magnetic resonance imaging protocol using said information in said database;
   convert each imaging goal into a plurality of first metrics and a range for each of said first metrics;
   obtain the protocol parameters assigned to the selected magnetic resonance imaging protocol from said database;
   determine a plurality of second metrics dependent on the protocol parameters obtained from said database, each second metric representing a calculated prediction of a corresponding first metric associated with the use of said protocol parameters obtained from said database;
   compare a range of each first metric with a range of the respective second metric determined therefrom;
   adjust the protocol parameters obtained from the database if one of said second metrics does not comply with the range of the respective first metrics from which said second metric was determined;
   operate a magnetic resonance data acquisition scanner so as to execute at least one selected magnetic resonance imaging protocol in order to acquire magnetic resonance raw data from a subject using the protocol parameters of said at least one selected magnetic resonance image protocol; and
   transform said acquired raw magnetic resonance data into magnetic resonance image data so as to reconstruct a magnetic resonance image that is needed for said image-guided radiotherapy.

4. The method as claimed in claim 1, comprising:
   via said computer, designating boundary conditions respectively for said plurality of first metrics; and
   adjusting the respective range of each of said first metrics according to said boundary conditions.

5. The method as claimed in claim 1, comprising:
   storing in the database a respective imaging goal that caused said at least one selected magnetic resonance imaging protocol to be selected, together with the selected magnetic resonance imaging protocol.

6. The method of claim 1, wherein each second metric is predicted using calculations based upon at least one of (i) physical models, and (ii) simulations.

7. The method of claim 1, wherein each second metric is predicted using calculations based upon physical laws.

\* \* \* \* \*